(12) United States Patent
Hazut et al.

(10) Patent No.: US 9,364,650 B2
(45) Date of Patent: Jun. 14, 2016

(54) METHOD FOR REMOVING PIGMENTS FROM A PIGMENTED SECTION OF SKIN

(75) Inventors: Aharon Hazut, Emek HaYarden (IL); Golan Fredi Hok, Hazor HaGalilit (IL)

(73) Assignee: Hawk Medical Technologies Ltd., Yokneam (IL)

( * ) Notice: Subject to any disclaimer, the term of this patent is extended or adjusted under 35 U.S.C. 154(b) by 427 days.

(21) Appl. No.: 10/560,063

(22) PCT Filed: Jun. 10, 2004

(86) PCT No.: PCT/IL2004/000497
§ 371 (c)(1),
(2), (4) Date: Dec. 8, 2005

(87) PCT Pub. No.: WO2004/107995
PCT Pub. Date: Dec. 16, 2004

(65) Prior Publication Data
US 2006/0142708 A1    Jun. 29, 2006

(30) Foreign Application Priority Data

Jun. 10, 2003 (IL) .......................................... 156374

(51) Int. Cl.
*A61M 37/00*     (2006.01)
*A61B 17/00*     (2006.01)
*A61F 13/02*     (2006.01)

(52) U.S. Cl.
CPC .. *A61M 37/0076* (2013.01); *A61B 2017/00769* (2013.01); *A61F 13/0203* (2013.01)

(58) Field of Classification Search
CPC ............... A61M 37/0076; A61B 2017/00769; A61F 13/0203

USPC ........ 606/186, 167; 81/9.22; 30/358; 602/41, 602/48
See application file for complete search history.

(56) References Cited

U.S. PATENT DOCUMENTS

| | | | |
|---|---|---|---|
| 4,588,400 A * | 5/1986 | Ring et al. | 604/304 |
| 4,858,604 A | 8/1989 | Konishi | |
| 5,019,596 A * | 5/1991 | Reiner et al. | 514/578 |
| 5,244,920 A * | 9/1993 | Reiner et al. | 514/554 |
| 5,271,943 A * | 12/1993 | Bogart et al. | 424/484 |
| 5,401,242 A | 3/1995 | Yacowitz | |

(Continued)

FOREIGN PATENT DOCUMENTS

| | | |
|---|---|---|
| FR | 983602 A | 6/1951 |
| GB | 2234420 A2 | 2/1991 |

(Continued)

OTHER PUBLICATIONS

Taylor CR, Anderson RR, Gange RW, Michaud NA, Flotte TJ. Light and electron microscopic analysis of tattoos treated by Q-switched ruby laser. J Invest Dermatol. Jul. 1991; 97(1):131-6.*

(Continued)

*Primary Examiner* — Thomas McEvoy
(74) *Attorney, Agent, or Firm* — Marsteller & Associates, P.C.

(57) ABSTRACT

The present invention relates to a method for removing pigments from a pigmented section of a skin by puncturing the skin at the pigmented section, with a skin puncturing device which is provided with at least one needle, and then bandaging the punctured section with a suitable adsorbing pad. The pad contains one or more materials, such as saline, which will cause the pigments at the punctured section to migrate into the outer layer of the skin.

2 Claims, 4 Drawing Sheets

(56) References Cited

U.S. PATENT DOCUMENTS

| | | | |
|---|---|---|---|
| 5,423,736 A * | 6/1995 | Cartmell et al. | 602/42 |
| 6,251,121 B1 | 6/2001 | Saadat | |
| 6,375,977 B1 * | 4/2002 | Auguste et al. | 424/447 |
| 6,432,114 B1 | 8/2002 | Rosso | |
| 6,607,513 B1 | 8/2003 | Down et al. | |
| 6,689,095 B1 | 2/2004 | Garitano et al. | |
| 6,692,456 B1 | 2/2004 | Eppstein et al. | |
| 6,743,211 B1 | 6/2004 | Prausnitz et al. | |
| 7,012,096 B2 * | 3/2006 | Dosch et al. | 514/557 |
| 7,314,470 B2 | 1/2008 | Malodobry | |
| 2002/0138049 A1 | 9/2002 | Allen et al. | |
| 2002/0183688 A1 | 12/2002 | Lastovich et al. | |
| 2004/0001878 A1 * | 1/2004 | DeBusk et al. | 424/445 |
| 2004/0111107 A1 * | 6/2004 | Malodobry | 606/186 |
| 2004/0158196 A1 * | 8/2004 | Garitano et al. | 604/68 |
| 2006/0142708 A1 | 6/2006 | Hazut et al. | |
| 2007/0156095 A1 | 7/2007 | Hazut et al. | |
| 2008/0031288 A1 * | 2/2008 | Sierra et al. | 372/12 |

FOREIGN PATENT DOCUMENTS

| | | | |
|---|---|---|---|
| JP | 2001293095 A2 | 10/2001 | |
| SU | 1109168 | 8/1984 | |
| WO | 9964580 | 12/1999 | |
| WO | 9964580 A1 | 12/1999 | |
| WO | 0064514 A | 11/2000 | |
| WO | 0074767 A2 | 12/2000 | |
| WO | 0076411 A2 | 12/2000 | |
| WO | 0236027 A2 | 5/2002 | |
| WO | 2004/107995 | 12/2004 | |

OTHER PUBLICATIONS

"Tattoo Removal". http://patient-info.com/tattoo.htm. Copyright 2000. p. 3—Salabrasion.

Eddy M. Van Der Velden et al, Tattoo Removal: Tannic Acid Method of Variot, Pharmacology and Therapeutics, pp. 376-380, vol. 5, No. 5, May 1993.

Gary H. Manchester, Tattoo Removal, The Western Journal of Medinice, pp. 10-12, vol. 118, Mar. 1973.

International Search Report for PCT/IL04/0497.

Written Opinion for PCT/IL04/0497.

International Preliminary Report on Patentability for PCT/IL04/0497.

Material Safety Data Sheet (MSDS) for Sodium Chloride ACS Reagent sold by Sigma-Aldrich, Feb. 1, 2006.

Material Safety Data Sheet (MSDS) for RNase-Free Buffer (5M NaCl) sold by Ambion, Inc. Jan. 10, 2006.

Takesue, M, Aichi Gakuin Daigaku Shigakkai Shi, 27 (1) :277-316, 1989, Effect of Caffeine on Wound Healing of the Rat Gingiva, abstract.

International Search Report published Mar. 10, 2005 for International Application No. PCT/IL2004/000784, filed Aug. 30, 2004.

Written Opinion published Mar. 1, 2006 for International Application No. PCT/IL2004/000784, filed Aug. 30, 2004.

International Preliminary Report on Patentability published Mar. 1, 2006 for International Application No. PCT/IL2004/000784, filed Aug. 30, 2004.

www.healthylivinganswers.com/skin-care/, Feb. 26, 2010m "layers of the skin-epidermis-dermis-hypodermis".

Final Office Action dated Oct. 27, 2009 in U.S. Appl. No. 10/569,525.

Office Action dated Nov. 28, 2008 in U.S. Appl. No. 10/569,525.

Lea P.J., and Pawlowski A., Human tattoo.Electron microscopic assessment of epidermis, epidermal-dermal junction, and dermis, Int J. Dermatol. Sep. 1987: 26(7): 453-8.

Graeme M. Lipper and R. Rox Anderson, "Lasers in Dermtology", p. 2508 from chapter 267, Fitzpatrick's Dermatology in General Medicine, sixth edition, 2003.

Office Action dated Jun. 19, 2009 for U.S. Appl. No. 10/569,525.

Notice of Allowance dated Nov. 10, 2010 for U.S. Appl. No. 10/569,525.

Taylor et al, Light and Electron Microscopic, J. Investigative Dermatology, p. 131-36, 1991.

Restriction Requirement dated Jun. 19, 2009 for U.S. Appl. No. 10/569,525.

\* cited by examiner

METHOD FOR REMOVING PIGMENTS FROM A PIGMENTED SECTION OF SKIN

FIELD OF THE INVENTION

The present invention relates to the field of pigments removal. More particularly, the invention relates to a method for removing pigments from a pigmented section of skin, preferably a tattoo.

BACKGROUND OF THE INVENTION

Tattoos are created by injecting ink into the skin. Today, in most cases, the injection of the ink is done by one or more needles which are attached to a device. Such a device will be called hereinafter a skin puncturing device. Preferably, but not limitatively, the skin puncturing device is a hand-held device. The skin puncturing device moves the needle along the longitudinal axis of the needle, similar to the movement of a needle in a sewing machine. Usually the skin puncturing device moves the needle at a rate of several vibrations per minute (e.g., the needles may puncture the skin at the rate of 50 to 3,000 times per minute). Prior to the penetration of the needle into the skin, the needle is dipped in a suitable solution which contains pigment (e.g., ink) and then this solution is sucked up through a suitable tube system of the skin puncturing device. Alternatively, the solution may be provided to the needle through a capsule suitable to be connected to the skin puncturing device. After obtaining the solution the skin puncturing device is used to puncture the top layer of the skin and to drive insoluble, micrometer-sized particles of ink into the dermal layer of skin (i.e., dermis), preferably, about one millimeter deep. As a result, the ink is not located in the epidermis, but it intermingles with cells in the dermis. Since the cells of the dermis are relatively fixed the tattoo's ink remains at the dermis, thereby tattooing the skin.

For a variety of reasons, there are people who wish to remove a tattoo from their skin. However, because tattoos are intermingled with cells in the dermis, removing them is not an easy task. In the prior art, several methods for removing tattoos exist, which methods are usually invasive, some of them even requiring surgery, and may also be painful. Such known methods are:

Dermabrasion, wherein skin is "sanded" (i.e., abraded) to remove the surface which contains the tattoo;
Cryosurgery, wherein the area where the tattoo is located is frozen prior to its removal; and
Excision, wherein the dermatologic surgeon removes the tattoo with a scalpel and closes the wound with stitches (In some cases involving large tattoos, a skin graft from another part of the body may be necessary).

However, such tattoo removal methods are painful, and may also create scars.

Other methods for tattoo removal use lasers. Lasers offer a bloodless alternative to the abovementioned methods and may also have fewer side effects. Each removal procedure is done or in a single or in a series of treatments. Patients may or may not require topical or local anesthesia. Lasers remove tattoos by producing short pulses of intense light that pass through the top layers of the skin, to be selectively absorbed by the tattoo pigment. This laser energy causes the tattoo pigment to fragment into smaller particles that are then removed by the body's immune system. However, there is still a possibility that using a laser may cause scarring. Furthermore, it is difficult to remove with the lasers pigments having colors such as yellow and green. Such colors selectively absorb laser light and can only be treated by selected lasers based on the pigment color. Moreover, there are side effects of laser procedures which may cause, for instance, hyperpigmentation, or an abundance of color in the skin at the treatment site, and hypopigmentation, where the treated area lacks normal skin color.

In addition, having a tattoo removed in each of the above methods is a long and expensive procedure.

All the methods described above have not yet provided satisfactory solutions to the problem of removing a pigmented section of skin in a simple way.

It is an object of the present invention to provide a method for removing a pigmented section of skin, which overcomes the drawbacks of the prior art.

It is another object of the present invention to provide a method for removing a pigmented section of skin which is relatively inexpensive.

Other objects and advantages of the invention will become apparent as the description proceeds.

SUMMARY OF THE INVENTION

The present invention relates to a method for removing pigments from a pigmented section of a skin, which comprises: a) providing a skin puncturing device which is provided with at least one needle; b) puncturing the skin at said pigmented section with said skin puncturing device, preferably—but not limitatively, while said skin puncturing device contains no ink and, optionally, injecting an aqueous material; c) providing a pad containing one or more materials capable of absorbing moisture from the mixture of said aqueous material with the pigments at said section, or absorbing moisture from the mixture of said pigments with the cellular fluids at said section; and d) bandaging said punctured skin with said pad, thereby causing the pigments at said section to migrate from their location toward the outer layer of the skin.

The term "aqueous mixture of tattoo ink" or "pigments" indicates a mixture of small particles with water, which may or may not include some dissolved pigments. The terms "ink" and "pigment" are used herein interchangeably.

According to a preferred embodiment of the present invention, the method further comprises applying one or more antiseptic and/or antibiotic materials to the punctured skin. Preferably, the one or more antiseptic and/or antibiotic materials are applied to the punctured area of the skin by bandaging said area with a pad containing said materials. Alternatively, the antiseptic and/or antibiotic materials are applied directly onto the punctured area of the skin.

Preferably, the skin puncturing device is an electric tattooing device.

According to a preferred embodiment of the present invention, each needle can be solid or hollow.

Preferably, the skin puncturing device is further provided with suction means.

According to another preferred embodiment of the present invention, the method further comprises, prior to the bandaging of the punctured skin and during the puncturing of said skin, performing suction of the pigments from said punctured skin by means of the suction means.

Preferably, the injecting of the aqueous material to the skin is performed by dipping the needle(s) in said aqueous material prior to the puncturing of the skin. According to a preferred embodiment of the present invention, the aqueous material is selected from the group consisting of saline, water or other suitable aqueous solution or liquid.

The present invention further relates to an adsorbent pad suitable to absorb moisture from an aqueous mixture of tattoo ink or other pigments. Preferably, the adsorbent pad further comprises one or more antiseptic and/or antibiotic materials.

BRIEF DESCRIPTION OF THE DRAWINGS

The above and other characteristics and advantages of the invention will be better understood through the following illustrative and non-limitative detailed description of preferred embodiments thereof, with reference to the appended drawings, wherein.

DETAILED DESCRIPTION OF PREFERRED EMBODIMENTS

Figure 1:
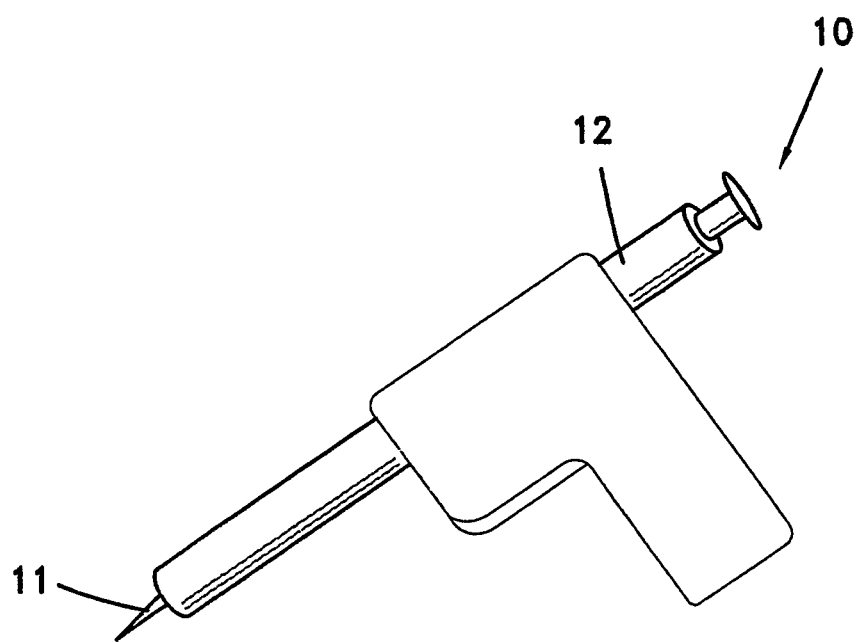
FIG. 1 schematically illustrates a skin puncturing device provided with suction means.

The present invention relates to a method for removing pigments from a pigmented section of a skin by puncturing the skin at the pigmented section and then bandaging the punctured section with a suitable adsorbing pad. The pad must contain one or more materials, such as saline, which are suitable to cause the pigments at the punctured section to migrate into the outer layer of the skin. Preferably, but not limitatively, the pad is an adsorbent pad suitable to absorb moisture from an aqueous mixture of tattoo ink. The aqueous mixture is generated at the punctured area either by cellular fluids or by the addition of an aqueous medium. Of course, the materials, which are suitable to cause the pigments at the punctured section to migrate and be absorbed into the outer layer of the skin, may be in the form of a solution, a solid material, or a combination of both a solution and a solid material.

According to a preferred embodiment of the present invention, the pad is designed such that it enables the aqueous mixture containing the tattoo ink to migrate into the outer layer of the punctured area of the skin. For example, the absorbent pad consists of a sterile, normal saline or salt-based granular paste, enclosed in a textile bag measuring 10 cm×10 cm.

The absorbent pad should be placed directly in contact with the surface of the punctured area, preferably—but not limitatively—covered with a suitable dressing such as a semi-permeable film. The aqueous mixture and cellular debris in the punctured area of skin are drawn into the pad. The pad should be removed before it is entirely saturated, when it is discolored with secretions, or after a given period of time, such that the saline will not cause damage to the skin. For example, a 3 gram pad sized 10 cm×10 cm provided with a 2.5 gram of saline should draw up about 5 grams of the aqueous mixture, within a period of less than 20 minutes.

Preferably, the absorbent material should be distributed equally within the pad or at least on one of its surfaces.

Of course, the adsorbent pad may contain one or more antiseptic and/or antibiotic materials, such as a benzalkonium chloride-based cream (e.g., Bepanthen), a silver sulfadiazine-based cream (e.g., Silverol) etc., or such antiseptic materials may be applied separately. For example, the adsorbent pad or other separate pad may contain pastes and/or creams known in the art, such as Vitamerfen, Bepanthen, Silverol and the like, or the antiseptic cream may be applied directly to the treated area and covered by a pad.

According to a preferred embodiment of the present invention, the skin can be punctured by a skin puncturing device which includes at least one needle, such as the one used for creating tattoos, while operating this device in the same way as is done while creating tattoos. As an option, an aqueous solution or other material that, preferably—but not limitatively—does not contain pigments, may be used instead of the ink (which is used when creating the tattoo), thereby allowing the pad containing one or more materials to absorb moisture from the mixture of the aqueous solution with the pigments that was generated at the punctured area. In cases when an aqueous solution is not used while puncturing the skin, the pad is capable of absorbing moisture only from the mixture of the pigments (e.g., tattoo ink) with the cellular fluids liberated at the punctured section. Preferably, but not limitatively, the aqueous solution is injected into the punctured area. For example, the injecting of the aqueous solution into the skin is performed by dipping the needle(s) of the skin puncturing device in the aqueous solution prior to the puncturing of the skin. The aqueous solution or material can be saline, water or other suitable aqueous solution or liquid.

In typical puncturing devices, the penetrating depth of the needle to the skin is adjustable. Preferably, but not limitatively, the needle does not penetrate beyond the hypodermis layer of the skin and thus no further damage to the skin is done while using the method of the present invention. Each needle of the skin puncturing device can be solid or hollow.

According to a preferred embodiment of the present invention, the skin puncturing device is further provided with suction means for performing a suction of the skin pigments during the puncturing activity of the skin. FIG. 1 schematically illustrates a skin puncturing device 10 provided with such suction means. The skin puncturing device 10 comprises suction means 12 coupled to needle 11 via the tube system (not shown) of the skin puncturing device 10.

According to a preferred embodiment of the present invention, the method involves "encouraging infection", which may aid the pigments to migrate to the outer layer of the skin. This can be treated by applying antibiotic material(s) to the punctured area of the skin, preferably, after removing the absorbent pad, and until most of the pigments are removed from that area of the skin. This activity can take from several hours to several days.

Figure 2A:
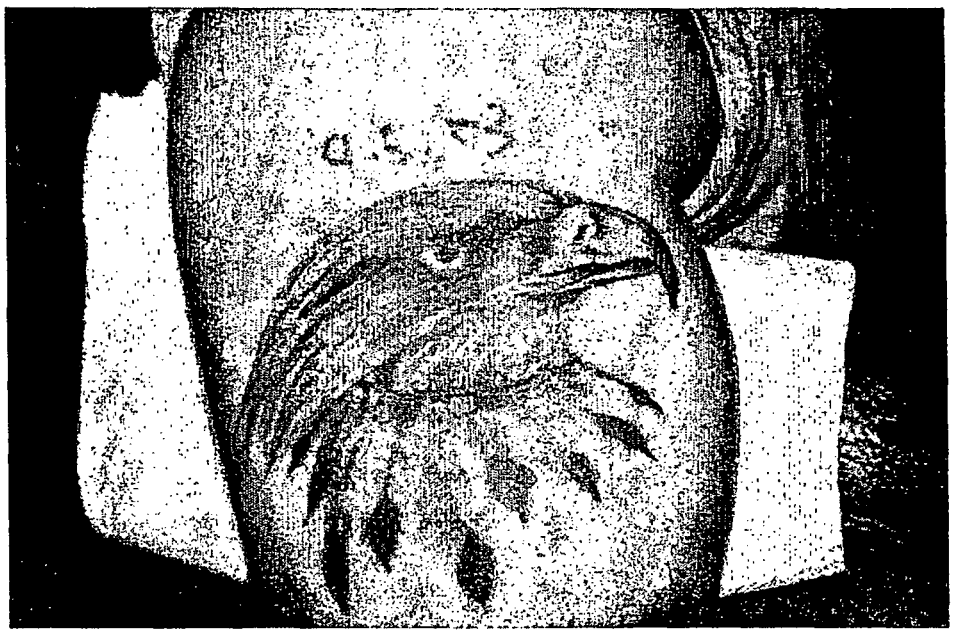
FIG. 2A is a photograph showing a head of an eagle being tattooed on a human arm.
Figure 2B:
FIGS. 2B and 2C are photographs showing the head of the eagle of FIG. 2A after part of it was removed by using the method of the present invention.
Figure 2C:

FIG. 2A is a photograph showing a head of an eagle tattooed on an arm. FIGS. 2B and 2C are photographs showing the head of the eagle of FIG. 2A after part of it (i.e., the tattooed feathers at the neck of the eagle) was removed by using the method of the present invention.

The above examples and description have of course been provided only for the purpose of illustration, and are not intended to limit the invention in any way. As will be appreciated by the skilled person, the invention can be carried out in a great variety of ways, employing more than one technique from those described above, all without exceeding the scope of the invention.

The invention claimed is:

1. A method for removing pigments from a pigmented section of skin, comprising:
   a) puncturing skin at said pigmented section with a skin-puncturing device provided with at least one needle, thereby liberating pigments and cellular fluids from within cells containing said pigments;
   b) providing a pad adapted to absorb the pigments and cellular fluids liberated by the puncturing, said pad containing one or more materials capable of accelerating a process of migration of said pigments toward an outer layer of the skin, wherein said one or more materials is a salt-based granular paste; and c) bandaging a surface of said punctured skin by placing the pad in direct contact with the surface of the punctured skin such that the one or more materials contained in the pad have direct contact with the surface of the punctured skin but remain contained within the pad.

2. The method according to claim 1, further comprising injecting an aqueous solution into the pigmented section during the puncturing of the skin.

* * * * *